United States Patent [19]
Huge

[11] 4,055,895
[45] Nov. 1, 1977

[54] INTRA-ORAL TOOTH POSITIONER AND PROCESS FOR PRODUCTION THEREOF

[75] Inventor: Gerald W. Huge, Racine, Wis.

[73] Assignee: Professional Positioners, Inc., Racine, Wis.

[21] Appl. No.: 671,876

[22] Filed: Mar. 29, 1976

[51] Int. Cl.² ............................................. A61C 7/00
[52] U.S. Cl. .................................. 32/14 B; 128/136
[58] Field of Search ..................... 32/7, 14 A–14 C, 32/66; 128/136, 137; 264/45.5

[56] References Cited

U.S. PATENT DOCUMENTS

| | | | |
|---|---|---|---|
| 3,223,085 | 12/1965 | Gores et al. | 128/136 |
| 3,724,075 | 4/1973 | Kesling | 32/14 B |
| 3,904,720 | 9/1975 | Sjostrand | 264/45.5 |

Primary Examiner—Russell R. Kinsey
Assistant Examiner—Mickey Yu
Attorney, Agent, or Firm—Wheeler, Morsell, House & Fuller

[57] ABSTRACT

One or more prestressed elastic bands is incorporated into a resilient tooth positioner (such as that described in U.S. Pat. Nos. 2,467,432 and 2,531,222) in such a manner that they bear on the buccal and labial surfaces of one or both arches of a patient's teeth. Such incorporation causes the tooth positioner to tend to contract while in place so that inward pressure is exerted on the teeth of one or both arches, closing spaces between the teeth. Such prestressed elastic bands may be incorporated into resilient tooth positioners by stretching pre-cured elastic bands along the arch of a cast of a patient's teeth (or along an arch-shaped generalized form) and maintaining such tension while molding identical or compatible uncured material around the teeth and bands and while curing such materials to complete the appliance. Such bands may also be attached to existing tooth positioners by various means, and bands having various configuration can be used.

12 Claims, 9 Drawing Figures

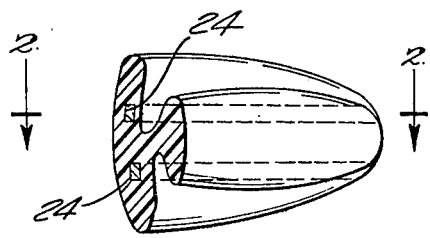
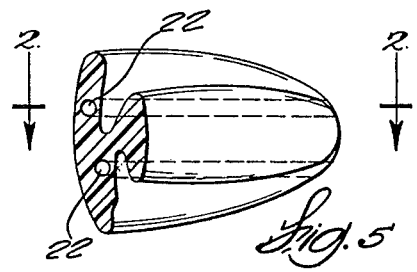
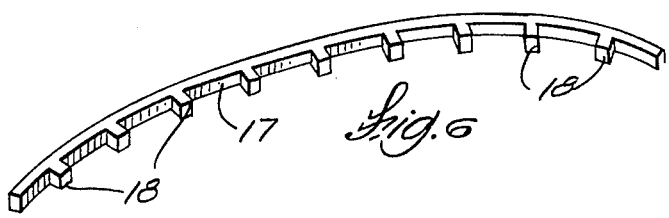
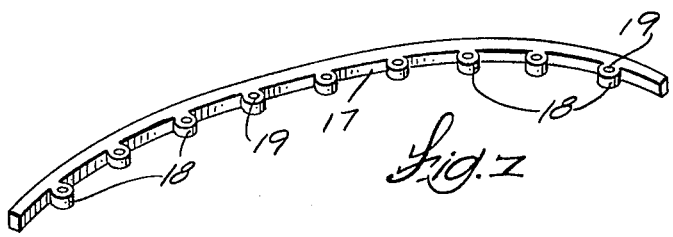
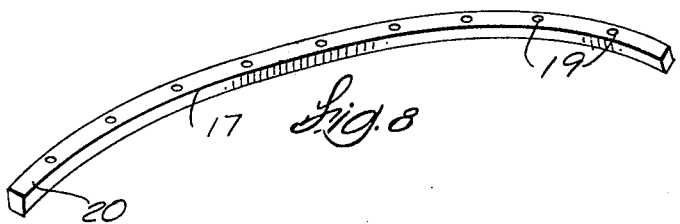

INTRA-ORAL TOOTH POSITIONER AND PROCESS FOR PRODUCTION THEREOF

DEFINITIONS

Elastic Band as used herein means a band which tends to contract in length when it is held in lengthwise tension, or prestressed. This includes elastic rubber or polymer strips, coil springs, and analogous devices suitable for dental use.

The buccal and labial surfaces of the teeth respectively adjoin the cheek and the lips, and are the outer surfaces of the teeth, or the side away from the tongue.

The lingual surface is the inner surface of a tooth or teeth, or the side facing the tongue.

Lingual pressure means pressure exerted in a direction tending to push the teeth inward, toward the tongue.

Pre-cured refers to material which is formable in an initial state, such as plastic or liquid, but can be treated to become resilient, and which has been so cured insofar as a curing process is necessary to form a resilient, elastic finished article. It further includes materials which need no curing to become capable of sustaining longitudinal tension, such as metal coil springs.

Pre-stressed means placed under lengthwise tension and held in tension until secured to a tooth positioner so that the tension is applied to the body of the tooth positioner.

SUMMARY OF THE INVENTION

In one aspect the invention herein claimed consists of an arch-shaped resilient tooth positioner which incorporates one or more prestressed members such as elastic bands extending along the convex side of the dental arch. The pre-stressed elastic bands exert a lingual pressure or force through the positioner on the buccal and labial surfaces of a patient's teeth. The use of prestressed elastic bands increases the amount of tension which may be applied using an arch-shaped resilient tooth positioner, and the bands also help to secure the tooth positioner to the patient's teeth when the appliance is worn, even after the patient's teeth have moved in response to the tooth positioner.

In another aspect the invention consists of a method to incorporate prestressed elastic bands into resilient archshaped tooth positioners, wherein precured elastic bands, made of material identical to (or compatible with) the material comprising the tooth positioner, are stretched over a cast or modified cast (called a set-up) of the patient's teeth and secured thereto. (An arch-shaped form can be substituted for the cast of a patient's teeth.) The prestressed member such as a precured plastic elastic band may be separated from the surface of the cast or form by means of spacing blocks. Uncured resilient material is molded around the cast and the bands to form a tooth positioner. Finally, the resilient material is cured, if required. This bonds the precured pre-stressed elastic bands to the tooth positioner. As a result, a tooth positioner is formed, consisting of pre-stressed bands incorporated in an unstressed resilient body. The shape of the band may be such as to aid in its retention in the tooth positioner, and may include projections, holes, or the coils of a spring.

Methods are also claimed whereby to attach prestressed elastic bands to existing tooth positioners. This may be accomplished by securing pre-stressed elastic bands to the inside concave surface of the tooth positioner. A second method by which to add prestressed elastic bands to tooth positioners is to form a passage in a tooth positioner which follows the curvature of the arch, so that a prestressed elastic band can be added to a tooth positioner later, should it become necessary. Such a passage or tunnel may be formed by placing a smooth cylindrical element that will not bond to the positioner material in a position adjacent the cast, set-up, or form in a path along the dental arch before molding the positioner, to serve as a core. After molding, the wire or other cylindrical element is removed, leaving a passage for later placement of an elastic band under stress longitudinally.

REFERENCE TO THE DRAWINGS

FIG. 4 is a view similar to FIG. 3, showing an embodiment having prestressed elastic bands in the interior thereof.

FIG. 5 is a view similar to FIG. 3, showing a passage into which a prestressed elastic band may be inserted after the tooth positioner has been formed.

FIG. 6 is a top perspective view of an elastic band having incorporated spacing elements.

FIG. 7 is a top perspective view of an elastic band incorporating perforated spacing blocks.

FIG. 8 is a top perspective view of an elastic band with perforations.

FIG. 9 is an elastic band consisting of a metallic coil spring.

DESCRIPTION AND SPECIFICATION

Although the disclosure hereof is detailed and exact to enable those skilled in the art to practice the invention, the physical embodiments herein disclosed merely exemplify the invention which may be embodied in other specific structure. While the best known embodiment has been described, the details may be changed without departing from the invention, which is defined by the claims.

Figure 1:
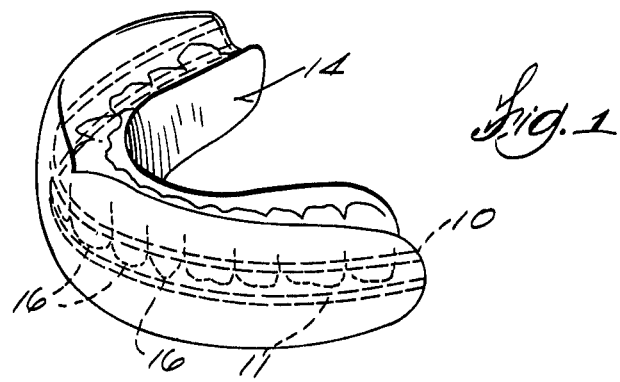
FIG. 1 is a top perspective view of a tooth positioner which contains one embodiment of the improvement described herein.
Figure 2:
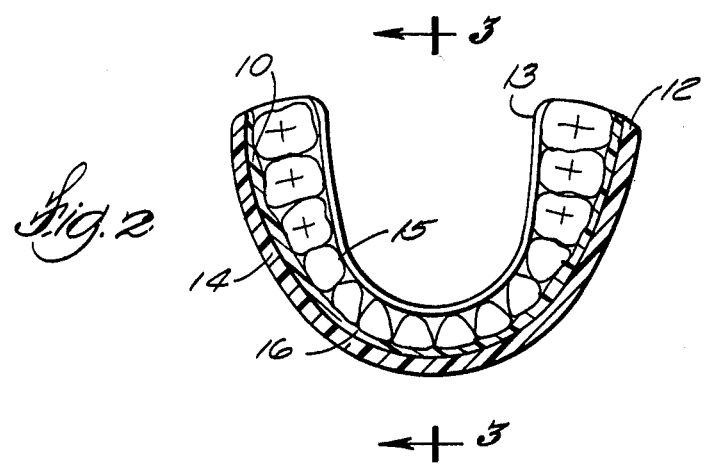
FIG. 2 is a top plan view of the tooth positioner shown in FIG. 1 broken away to line 2—2 in FIGS 3–5.
Figure 3:
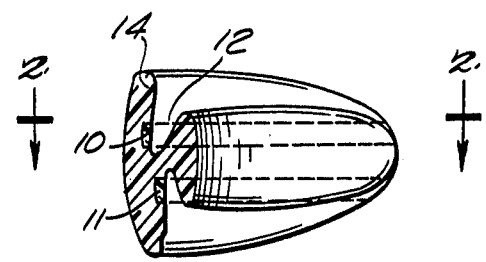
FIG. 3 is a cross-sectional view taken along the line 3—3 in FIG. 2, showing prestressed elastic bands incorporated at the surface of the tooth positioner.

Referring now in detail to FIGS. 1, 2 and 3: tooth positioner 14, which may be designed to enclose the teeth of either one of both arches, has a substantially concave wall 12 bearing lingually on the buccal and labial surfaces 16 of the patient's teeth, and a substantially convex wall 13 adjacent to the lingual surface of the teeth.

One or more prestressed elastic bands such as 10 and 11 are secured to the concave wall 12 in such a manner that they bear on the buccal and labial surfaces of the teeth in a lingual direction when the appliance is worn. Such bands may also be secured wholly inside the tooth positioner, as shown at 24 in FIG. 4.

The concave surface 12 consists of impressions of the buccal and labial surfaces of one arch of the patient's teeth and convex surface 13 consists of impressions of the lingual surfaces corresponding to the buccal and labial impressions.

FIGS. 6, 7, 8 and 9 show various elastic bands usable in the invention. In FIGS. 6 and 7, spacing blocks 18 lie on side 17 of the elastic band, which faces the teeth.

These blocks 18 may press on certain teeth selectively, or they may be used to hold the band away from the cast of teeth in the method of formation described below. In FIGS. 7 and 8, perforations 19 (preferably vertical) passing through the spacing blocks 18 (FIG. 7) or the body of the prestressed elastic band (FIG. 8) facilitate anchoring of the prestressed elastic band to the body of the tooth positioner. FIG. 9 shows an elastic band consisting of a metallic coil spring. If the spring is stretched or pre-stressed sufficiently, the coils separate and permit the material of the body of the tooth positioner to enter while it is being formed, locking the pre-stressed band into position.

One method which may be used to manufacture my tooth positioners containing prestressed elastic bands is as follows.

First, bands of elastic material which have already been cured (if necessary), including but not limited to the identical material used to make the balance of the tooth positioner, are stretched to a length giving sufficient tension along the arch of a cast of the patient's teeth. The cast may be a replica of the patient's arch of teeth, a set-up model of the teeth which has been modified so that the teeth of the cast are in more favorable positions from the orthodontic view-point, or an arch-shaped form. Tension is maintained on the elastic bands throughout the manufacturing process, such as by securing overlapping parts of the band adhesively or mechanically to the cast or to a mold form containing the cast.

Second, uncured and unstressed material is built up around the arch or arches of the cast in order to form the tooth positioner in a known way. Liquid urethane and uncured rubber are suitable materials. This material contacts the exposed surfaces of the prestressed elastic band in intimate juxtaposition. If the prestressed elastic band has irregularities such as blocks 18 (FIGS. 6 and 7), perforations 19 as (FIGS. 7 and 8) or coils (FIG. 9) above described, uncured material will flow in to anchor the prestressed elastic band in place. Finally, the material comprising the balance of the tooth positioner is appropriately cured. The material used for the bands, being either identical to or bondably compatible with the material of the positioner, becomes permanently bonded to the body of the tooth positioner.

Elastic bands may also be attached to the inside concave surface of an existing tooth positioner, or inside an internal passage formed in the body of tooth positioner, which passage generally follows the arch-shaped contour of the tooth positioner. Such passages, depicted in FIG. 5, can conveniently be incorporated into a tooth positioner as it is formed by replacing the compatible prestressed elastic band with an incompatible smooth-sided band, such as a wire, in the above process. This incompatible band is later removed by pulling it out from one end, leaving a passage 22 through which an elastic band may be inserted, pre-stressed, and bonded using a material bondable or curable to adhere to the positioner body, or the ends may be secured in position at the ends of the passage.

As a result of any of these methods a tooth positioner is formed, consisting of an unstressed body bonded permanently to prestressed elastic bands.

I claim:

1. Tooth positioner means comprising an unstressed archshaped body of resilient material formed to fit within a patient's mouth between the upper and lower arches, such means having a generally concave surface bearing on the buccal and labial surfaces of the teeth of at least one arch and having a convex surface adjacent to the lingual surface of the teeth of said arch, and such means having at least one prestressed elastic band which exerts lingual force on the buccal and labial surfaces of the teeth of at least one arch when the tooth positioner is worn.

2. The invention in claim 1, where the prestressed elastic band has at least one vertical perforation.

3. The invention in claim 1, where the concave surface of the tooth positioner means consists of impressions of the buccal and labial surfaces of at least one arch of the patient's teeth, and where the convex surface of the tooth positioner consists of impressions of the lingual surfaces corresponding to said buccal and labial impressions.

4. The invention of claim 1, wherein said prestressed elastic band consists of the same elastic material as the body of the tooth positioner.

5. The invention of claim 1, wherein said prestressed elastic band consists of coil springs.

6. The invention in claim 1, where said prestressed elastic band are mechanically attached to the inside concave surface of a complete tooth positioner.

7. The invention in claim 1, where said prestressed elastic band is attached inside an interior passage which follows the arch-shaped contour of a completed tooth positioner.

8. A process to bond at least one prestressed elastic band to tooth positioner means, comprising the steps of:
placing one or more pre-cured elastic bands under longitudinal tension along the buccal and labial surface of the line of teeth in a dental arch-shaped model, maintaining such position and tension of the bands throughout the process;
applying to said cast and bands uncured resilient material to form the tooth positioner means; and
curing the uncured material whereby to form a tooth positioner comprised of prestressed and unstressed portions.

9. The invention in claim 8, where spacing blocks are placed between the prestressed elastic bands and the teeth in the model before the uncured resilient material is applied to the model.

10. The invention in claim 9, where at least one of the spacing blocks has at least one vertical perforation.

11. The invention in claim 9, where the spacing blocks and the prestressed elastic bands are unitary.

12. The invention in claim 9, where spacing blocks are placed against selected teeth to increase the pressure applied to them.

* * * * *